United States Patent

Odneal et al.

Patent Number: 5,085,236
Date of Patent: Feb. 4, 1992

[54] DENTAL FLOSS MACHINE

[76] Inventors: Billie L. Odneal, 309 Telegraph Rd., Apt. #3, Pontiac, Mich. 48053; Charles S. Seidel, 436 Girard St., Royal Oak, Mich. 48087

[21] Appl. No.: 637,320

[22] Filed: Jan. 3, 1991

[51] Int. Cl.⁵ .............................................. A61C 15/00
[52] U.S. Cl. ..................... 132/325; 132/324; 132/322
[58] Field of Search ............... 132/324, 323, 325, 326, 132/327, 322

[56] References Cited

U.S. PATENT DOCUMENTS

| | | |
|---|---|---|
| 2,381,530 | 8/1945 | Dembenski ................ 132/325 |
| 2,492,291 | 12/1949 | Johnson . |
| 3,421,524 | 1/1969 | Waters . |
| 3,472,247 | 10/1969 | Borsum et al. . |
| 3,534,745 | 10/1970 | Waters ................ 132/322 |
| 3,592,203 | 7/1971 | Johnson ................ 132/323 |
| 3,667,483 | 6/1972 | McCabe . |
| 3,734,107 | 5/1973 | Thierman ................ 132/325 |
| 3,759,274 | 9/1973 | Warner . |
| 3,847,167 | 11/1974 | Brien . |
| 3,882,879 | 5/1975 | Lucas ................ 132/326 |
| 3,927,687 | 12/1975 | Thierman ................ 132/325 |
| 4,014,354 | 3/1977 | Garrett . |
| 4,031,908 | 6/1977 | Ting . |
| 4,235,253 | 11/1980 | Moore . |
| 4,245,658 | 1/1981 | Lecouturier . |
| 4,265,257 | 5/1981 | Salyer . |
| 4,307,740 | 12/1981 | Florindez et al. . |
| 4,319,595 | 3/1982 | Ulrich . |
| 4,326,549 | 4/1982 | Hinding . |
| 4,338,957 | 7/1982 | Meibauer . |
| 4,458,702 | 7/1984 | Grollimund . |
| 4,518,000 | 5/1985 | Leverette ................ 132/325 |
| 4,586,521 | 5/1986 | Urso . |
| 4,605,025 | 8/1986 | McSpadden . |
| 4,637,412 | 1/1987 | Martinez . |
| 4,706,695 | 11/1987 | Urso . |
| 4,830,032 | 5/1989 | Jousson . |
| 4,883,080 | 11/1989 | Lang . |

Primary Examiner—John J. Wilson
Assistant Examiner—Jeffrey A. Smith
Attorney, Agent, or Firm—Brooks & Kushman

[57] ABSTRACT

A dental flossing attachment 10 which imparts oscillatory motion to a strand of dental floss 19 inserted between the teeth. The attachment is adapted to mount on a drive shaft 14 of an electric tooth brush. The attachment has a housing 11 which contains a supply spool 18 and a take-up spool 21. An advancing mechanism is provided whereby fresh floss 19 may be positioned between two prongs 16 at the end of the housing 11 by turning a knob 22 without the need for manual threading of the dental floss through grooves or eyelets. When fresh dental floss is exhausted, the used attachment 10 is removed from the drive shaft 14 and a new attachment 10 is snapped into its place.

7 Claims, 3 Drawing Sheets

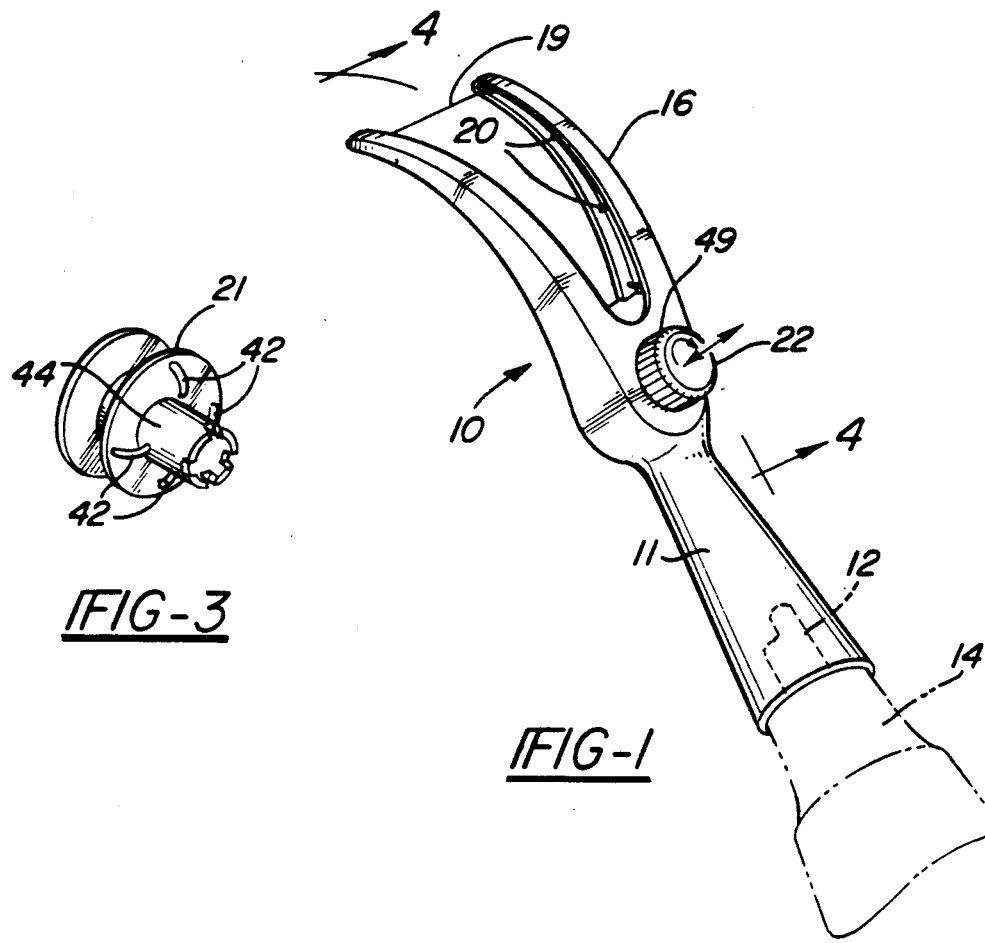
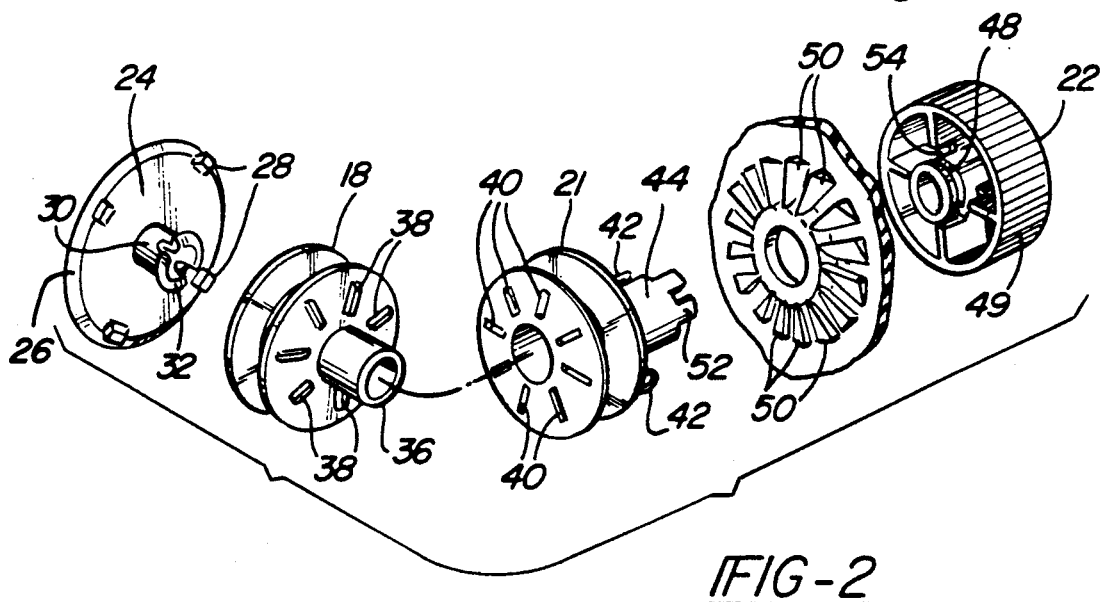

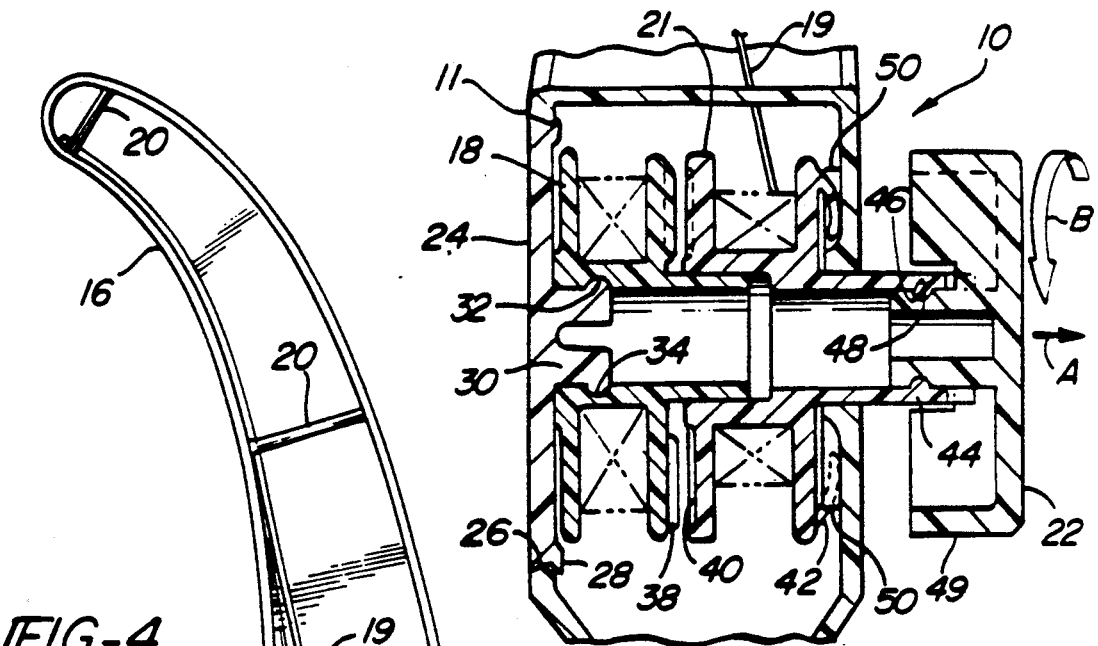
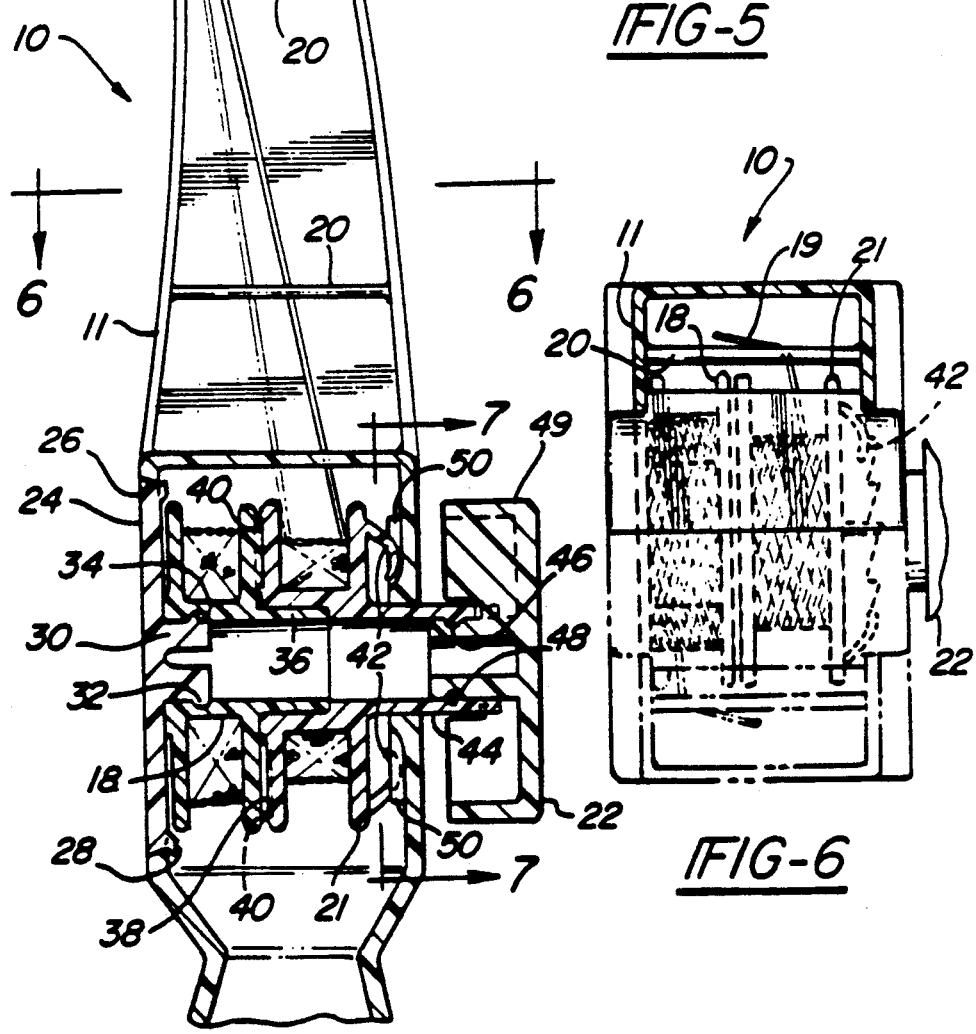

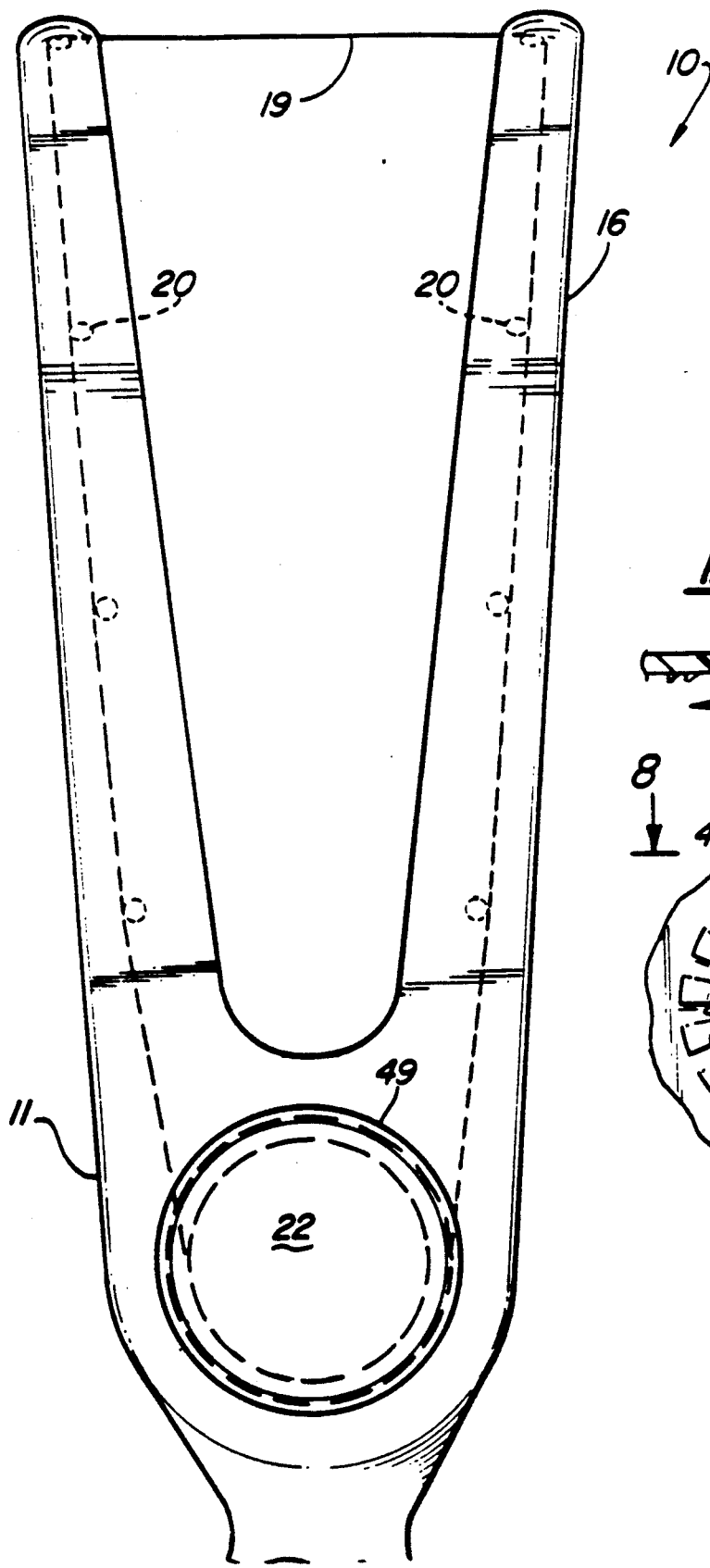
FIG-9
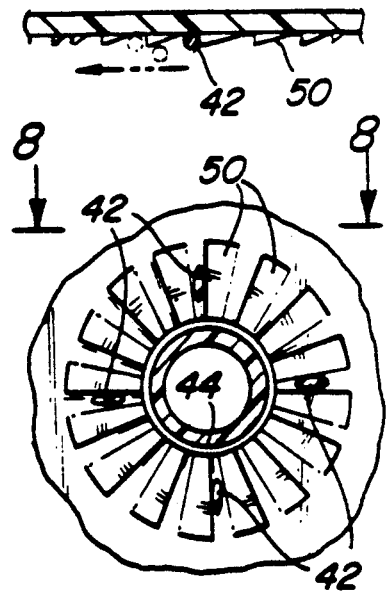
FIG-8
FIG-7

DENTAL FLOSS MACHINE

TECHNICAL FIELD

The present invention relates to an attachment for dental flossing which is removably attached to an electric toothbrush drive shaft for oscillatory motion, and has simplified means for advancing fresh dental floss onto the working portion of the apparatus.

BACKGROUND ART

Proper dental hygiene requires not only brushing of the exposed surfaces of teeth but also clearing interdental spaces between adjacent teeth. Failure to clear deposits from these hidden surfaces may result in excessive tooth decay. Even worse, naturally occurring bacteria in the mouth can act on deposited food particles between the teeth causing plaque which can eventually result in destructive periodontal disease.

Periodontal disease, in many instances, may be avoided through regular dental flossing. Until recently, this was accomplished by winding a length of dental floss around one finger of each hand and inserting the span of floss held between the fingers into the interdental space. This could prove very cumbersome as it often involved insertion of parts of one or both fists into the mouth. Various floss holders or frames have been designed to address this problem. The holders or frames may be driven by electrically generated oscillatory motion. However, a compact and easy to use automatic dental flossing device having a convenient floss advancing mechanism was not available.

U.S. Pat. No. 4,235,253 which issued to Moore discloses a device having a forked end on which a short strand of fresh dental floss is tightly secured. One disadvantage of this device is that the user must manually replace the strand of floss each time he desires a fresh length.

Improvements in this general concept have included different approaches to mounting spools on the device to provide for advancement of fresh floss. The problem with many of these devices is that during initial set up or replacement of spools, the user must thread a length of dental floss through a tortuous series of enclosures, recesses and eyelets. U.S. Pat. No. 4,458,702, issued to Grollimund and U.S. Pat. No. 4,706,695, issued to Urso disclose devices having this drawback. The device disclosed in U.S. Pat. No. 3,534,745, issued to Waters dispenses with the need for intricate floss threading but requires the user to open a small hinged door before turning a hand knob to advance the floss.

In general, all of the above prior art devices are cumbersome, and lack features necessary for effective interdental cleaning. Accordingly, it is an object of the present invention to provide an effective dental flossing apparatus having a means whereby oscillatory motion may be imparted to the working section of the dental floss.

It is another object of the present invention to eliminate the need for a user to manually handle or thread a length of dental floss.

It is a further object of the present invention to provide a simple one step method for advancement of fresh dental floss to the working portion of the apparatus.

It is still another object of the present invention to provide a small, lightweight flossing attachment which fits easily into the user's mouth, and can access difficult-to-reach molars.

It is another object of the present invention to provide a disposable flossing attachment for improved hygiene.

The above problems are solved by the flossing attachment of the present invention. Other objects and advantages of the invention are summarized below and described with reference to the drawings.

DISCLOSURE OF INVENTION

The present invention relates to a dental flossing attachment, which mounts on any commercially available electric toothbrush power unit and comprises an elongated housing having a receptacle at the power attachment end and a pair of spaced prongs at another end. A supply spool is mounted for rotation about an axis on an intermediate portion of the housing and a take-up spool is separably connected to the supply spool for rotation about the axis independently of the supply spool. Means are provided for engaging the supply spool with the housing for preventing rotation. Means are also provided for selectively engaging the take-up spool with the supply spool and thereby preventing relative movement between the two spools. When relative rotation is desired, such as when fresh floss is to be advanced, the take-up spool is disengaged from the supply spool and rotated independently, thereby pulling floss from the supply spool and across the ends of the spaced prongs.

Further advantages and features of the present invention are described in detail in the following detailed description in view of the attached drawings.

BRIEF DESCRIPTION OF DRAWINGS

FIG. 1 is a perspective view of the dental flossing attachment of the present invention shown attached to an electric toothbrush power unit;

FIG. 2 is an exploded perspective view of the floss spools and floss advance mechanism of the present invention;

FIG. 3 is a detailed perspective view of a floss take-up spool of the present invention;

FIG. 4 is a cross-sectional view taken along the line 4—4 of FIG. 1 showing the take-up spool engaged to a supply spool of the present invention;

FIG. 5 is a fragmentary cross-sectional view taken along the line 4—4 of FIG. 1 showing a knob of the present invention retracted in the direction of Arrow A, and the floss take-up spool disengaged from the supply spool;

FIG. 6 is a view along line 6—6 of FIG. 4 showing the floss spools in engagement;

FIG. 7 is a cross-sectional view taken along the line 7—7 of FIG. 4;

FIG. 8 is a view taken along the line 8—8 of FIG. 7; and

FIG. 9 is a plan view of floss holding prongs of the present invention.

BEST MODE(S) FOR CARRYING OUT THE INVENTION

Referring now to FIG. 1, the dental flossing apparatus of the present invention is illustrated. The flossing attachment 10 includes a housing 11 having a pair of spaced prongs 16 at one end and a receptacle 12 at another end. The receptacle 12 is removably connected to a drive shaft 14. The drive shaft 14 could be any one of a number of commercially available electric toothbrush power attachments. It is preferred that the electric toothbrush has a reduced speed capability for operating in a flossing mode.

Referring now to FIGS. 2, 3, and 4, the components and general function of the flossing attachment can be more readily observed. Mounted inside the housing 11 are a supply spool 18 and a take-up spool 21. A supply of dental floss 19 is wound around supply spool 18, extends to the prongs 16 and returns to the take-up spool 21. As shown in FIG. 9, the floss 19 is constrained to follow the path of the prongs 16 by studs 20 located at various intervals along the length of each prong 16. A knob 22, connected to the take-up spool 21, advances the dental floss 19 across the prongs 16 when the user desires to replace a used length of dental floss 19 with a fresh length. When all of the floss 19 has been used and advanced to the take-up spool 21, the entire attachment 10 is removed from the drive shaft 14. Then a new flossing attachment 10, preloaded with floss 19 in the manner above described, is simply snapped onto the drive shaft 14. Because the attachment 10 is designed to be loaded with floss 19 upon delivery to the user, there is never any need for the user to manipulate the floss 19 other than by knob 22. While this is a general description of the invention, a more specific description of the construction and interaction of the components follows.

The housing 11 which supports the components of the invention is structurally rigid. It may be inexpensively molded as a single piece out of a thermoplastic material. Being formed out of plastic affords other advantages such as the ability to form snapping fits with other components which also can be made out of plastic. For example, the receptacle 12 is removably snap fitted onto the drive shaft 14 so that when fresh floss is exhausted, it is easy for the user to pull off the used housing and snap on a replacement. Replacing the entire housing 11 in this manner provides fresh floss and a clean, hygienic housing 11.

When the flossing attachment 10 is in use, it is important to maintain tension of dental floss 19. This is accomplished by selectively restraining the supply spool 18 and take-up spool 21 in the following manner. First, the supply spool 18 frictionally engages and is held motionless by a base 24. The base 24 is disc-shaped and has a beveled rim 26. Along the rim 26 are a series of tabs 28. The tabs 28 and the beveled rim 26 combine to form a V-shape at their juncture which assists in snap fitting the base to the housing 11. Base 24 has an axial annular portion 30 which interfaces with the supply spool 18. As supply spool 18 slides over the annular portion 30, projections 32 engage a channel 34 on the inside wall of the supply spool 18. When this engagement is made, the supply spool 18 is seated on the base 24 and no relative axial movement of the two parts is permitted. In addition, the pressure exerted by the projections 32 on the inside wall of the supply spool 18 prevents rotational movement of the supply spool 18 relative to the base 24. The frictional holding force of the projections 32 may be overcome by application of rotary force on the knob 22 by the user as will be explained below.

With the supply spool 18 anchored to the housing 11, the take-up spool 21 engages the supply spool in the following manner. The supply spool 18 has an axial tube 36 which can be slidingly engaged with the inner surface of the take-up spool 21. When the take-up spool 21 is fully seated on the supply spool 18, a series of radially elongated and axially extending protrusions 38 and radially extending recesses 40 become engaged and prevent relative rotational movement of the take-up spool 21 and the supply spool 18. The interlocking configuration of the spools 18 and 21 is maintained by the pressure of spring members 42 which bias the take-up spool 21 toward supply spool 18.

The above configuration will prevent relative and absolute movement of the spools 18 and 21 under most circumstances thereby maintaining tension on the dental floss 19. However, after a period of use, the user will desire to advance a fresh supply of dental floss 19 between the prongs 16. This advance is accomplished by using knob 22 to unseat the take-up spool 21 and rotate it with enough force to overcome the spring pressure of projections 32 on the supply spool 18. Knob 22 slidingly receives an axial core 44 of the take-up spool 21. Knob 22 and take-up spool 21 are snap fitted together by the engagement of bumps 46 with groove 48 located on the knob 22. This engagement prevents relative axial movement between the knob 22 and the take-up spool 21. Relative radial movement between knob 22 and take-up spool 21 is prevented by a series of interlocking flutes 52 and slots 54.

Referring now to FIGS. 4 and 5, when the user pulls on the knob 22 in the direction of arrow A, spring members 42 are compressed as the take-up spool 21 is disengaged from the supply spool 18. Once disengaged, the take-up spool 21 may be rotated relative to the supply spool 18 subject only to the frictional pressure of projections 32 which tend to hold the supply spool 18 motionless. This frictional pressure is overcome by rotating the knob in the direction of arrow B. The rotation of knob 22 is aided by a plurality of striations 49 along the periphery thereof. Two or three rotations of the knob 22 should be sufficient to place a fresh length of floss 19 across the span of the prongs 16. Disposed on the underside of the housing 11 are a series of wedges 50 which contact the spring members 42.

FIGS. 7 and 8 illustrate the manner in which the spring members 42 are spaced to fit between the wedges 50. When knob 22 is rotated in the direction of Arrow B, the spring members 42 "ramp up" the sides of the wedges 50. Rotation is unidirectional because the vertical faces of the wedges 50 resist counter rotation. When sufficient dental floss 19 has been advanced to the prongs 16, the user may simply let go of the knob 22, thereby allowing the spring members 42 to once again bias the take-up spool 21 onto the supply spool 18.

The apparatus of the present invention has been described with reference to a preferred embodiment and is to be understood as being exemplary. Various changes and modifications are possible to the apparatus above within the spirit and scope of the present invention. The scope of the present invention should be determined by reference to the following claims.

I claim:

1. A dental flossing attachment for a power toothbrush having an oscillating drive shaft comprising:
   an elongated housing having a receptacle at a first end removably connected to the drive shaft;
   a pair of spaced prongs at a second end of the housing;
   a supply spool mounted for rotation about an axis on an intermediate portion of said housing between said first and second ends;
   a take-up spool separately connected to said supply spool for rotation about said axis independently of said supply spool and being selectively locked to said supply spool;

a supply of dental floss wound around said supply spool and extending from said supply spool to said second end between said spaced prongs and to said take-up spool;

means for holding floss tightly between said pair of prongs wherein said supply spool is held against rotation; and means located between a face of said take-up spool and said housing for biasing said take-up spool into engagement with said supply spool.

2. A dental floss attachment for a power toothbrush having an oscillating drive shaft comprising;

an elongated housing having a receptacle at a first end removably connected to the drive shaft;

a pair of spaced prongs at a second end of the housing;

a supply spool mounted for rotation about an axis on an intermediate portion of said housing between said first and second ends;

a take-up spool separably connected to said supply spool for rotation about the axis independently of said supply spool and being selectively locked to said supply spool;

a supply of dental floss wound around said supply spool and extending from said supply spool to said second end between said spaced prongs and to said take-up spool;

means operatively engaging said supply spool and said housing for resisting rotation of said supply spool with respect to said housing comprising at least one projection disposed on an annular portion of said housing, said at least one projection biased against an inside surface of said supply spool to develop holding pressures on said inside surface;

means operatively engaging said supply spool and said take-up spool for interlocking said take-up spool and said supply spool to selectively prevent rotation of said take-up spool with respect to said supply spool;

means for disengaging said take-up spool from said supply spool allowing the take-up spool to rotate independently of the supply spool to pull dental floss from said supply spool and through said spaced prongs; and means for advancing dental floss from said supply spool to said prongs.

3. The dental floss attachment of claim 2 wherein said at least one projection is an integral part of said annular portion of said housing.

4. A dental flossing attachment for a power toothbrush having an oscillating drive shaft comprising:

an elongated housing having a receptacle at a first and removably connected to the drive shaft;

a pair of spaced prongs at a second end of the housing;

a supply spool mounted for rotation about an axis on an intermediate portion of said housing between said first and second ends;

a take-up spool separably connected to said supply spool for rotation about the axis independently of said supply spool and being selectively locked to said supply spool;

a supply of dental floss wound around said supply spool and extending from said supply spool to said second end between said spaced prongs and to said take-up spool;

means operatively engaging said supply spool and said housing for resisting rotation of said supply spool with respect to said housing;

means operatively engaging said supply spool and said take-up spool for interlocking said take-up spool and said supply spool to selectively prevent rotation of said take-up spool with respect to said supply spool comprising at least one protrusion on a face of one of said spools, at least one recess on a confronting face of the other said spool and a biasing means holding said spools in engagement;

means for disengaging said take-up spool from said supply spool allowing the take-up spool to rotate independently of the supply spool to pull dental floss from said supply spool and through said spaced prongs; and means for advancing dental floss from said supply spool to said prongs.

5. The dental flossing attachment of claim 4 wherein said biasing means comprises a plurality of spring members disposed between a non-confronting face of said take-up spool and said housing.

6. The dental flossing attachment of claim 4 wherein each of said at least one protrusion comprises a radially elongated and axially protruding rib formed on said confronting face of said supply spool and each of said at least one recess comprises a corresponding radially extending slot on said confronting face of said take-up spool.

7. A dental flossing attachment for a power toothbrush having an oscillating drive shaft comprising:

an elongated housing having a receptacle at a first end removably connected to the drive shaft;

a pair of spaced prongs at a second end of the housing;

a supply spool mounted for rotation about an axis on an intermediate portion of said housing between said first and second ends;

a take-up spool separably connected to said supply spool for rotation about the axis independently of said supply spool and being selectively locked to said supply spool;

a supply of dental floss wound around said supply spool and extending from said supply spool to said second end between said spaced prongs and to said take-up spool;

means operatively engaging said supply spool and said housing for impeding rotation of said supply spool with respect to said housing;

means operatively engaging said supply spool and said take-up spool for interlocking said take-up spool and said supply spool to selectively prevent rotation of said take-up spool with respect to said supply spool; and means for disengaging said take-up spool from said supply spool allowing the take-up spool to rotate independently of the supply spool to pull dental floss from said supply spool and through said spaced prongs comprising a spring member and a knob affixed to said take-up spool, said knob translatable along the axis and overcoming said spring member biasing, thereby separating said take-up spool and said supply spool; and means for advancing dental floss from said supply spool to said prongs.

* * * * *